United States Patent [19]

Laugier et al.

[11] Patent Number: 5,190,936
[45] Date of Patent: Mar. 2, 1993

[54] PROCESS FOR IMPROVING THE THERAPEUTIC EFFICACY OF FAT-SOLUBLE CORTICOSTEROIDS AND COMPOSITION FOR CARRYING OUT THIS PROCESS

[75] Inventors: Jean-Pierre Laugier, Antony; Evelyne Segot, Nogent-sur-Marne; Francois Ringenbach, Bourg-la-Reine; Jean-Thierry Simonnet, Paris; Philippe M. Touzan, Vanves, all of France

[73] Assignee: L'Oreal, Paris, France

[21] Appl. No.: 536,891

[22] Filed: Jun. 13, 1990

[30] Foreign Application Priority Data

Jun. 15, 1989 [FR] France .................. 89 07947

[51] Int. Cl.$^5$ .................. A61K 31/56; A61K 37/22
[52] U.S. Cl. .................. 514/169; 424/450; 424/455
[58] Field of Search ........... 424/450, 455; 514/169, 514/177

[56] References Cited

U.S. PATENT DOCUMENTS 4,217,344 8/1980 Vanlerberghe et al. ............ 424/60
4,772,471 9/1988 Vanlerberghe et al. ............ 424/450

FOREIGN PATENT DOCUMENTS 2189457 10/1987 United Kingdom .

OTHER PUBLICATIONS

STN International File Server (Karlsruhe) & Chemical Abstracts. vol. 104, No. 17, Apr. 28, 1986, No. 142371m.
French Search Report on FR 89 07947.

*Primary Examiner*—Leonard Schenkman
*Assistant Examiner*—T. J. Criares
*Attorney, Agent, or Firm*—Cushman, Darby & Cushman

[57] ABSTRACT

The process consists in dissolving a corticosteroid in the lipid phase of nonionic amphiphilic lipid vesicles consisting of one or more lipid lamellae.

Composition for carrying out the above process, in which the vesicles are dispersed in an aqueous phase D, have an average diameter of between 10 and 5,000 nm and contain as corticosteroids 17- and/or 21-mono- or -diesters of hydrocortisone, cortisone, prednisone, prednisolone or 6-methylprednisolone, the corticosteroids representing 0.5 to 2.5% by weight of the total lipids of the lamellae.

21 Claims, No Drawings

PROCESS FOR IMPROVING THE THERAPEUTIC EFFICACY OF FAT-SOLUBLE CORTICOSTEROIDS AND COMPOSITION FOR CARRYING OUT THIS PROCESS

The present invention relates to a process for improving the therapeutic efficacy of corticosteroids and to a composition for carrying out this process.

Corticosteroids are hormonal derivatives extracted from the cortex of the adrenal capsules or obtained synthetically, and which contain a cyclopentanophenanthrene ring-system. They are antiinflammatory agents used, in particular, in the treatment of certain skin diseases, such as contact eczema or atopic dermatitis. In this case, the corticosteroids are generally used in the form of an ointment mixed with fats, and are applied topically at fairly large doses frequently producing adverse side effects such as cutaneous atrophy and depigmentation.

To avoid the adverse side effects, an effort is hence made, for a given therapeutic treatment, to use the smallest possible amounts of corticosteroids. One of the ways of obtaining this result consists in improving the therapeutic efficacy of a corticosteroid so that it is as high as possible for a specified dose. Any improvement in this therapeutic efficacy is very important, since it enables treatments to be prolonged and hence increases the chances of cure of the disease under treatment.

It is, moreover, known that some lipids, on dispersion in an aqueous phase, are capable of forming vesicles consisting of one or more lipid lamellae arranged approximately concentrically and encapsulating an aqueous phase. In the case where the vesicles are prepared from nonionic amphiphilic lipids, nonionic vesicles are obtained; in the case where ionic amphiphilic lipids are used, liposomes are obtained. Nonionic vesicles, as well as a process for preparing them, are described, for example, in Patent FR-A-2,315,991. In a known manner, the vesicles encapsulate an aqueous phase E and are dispersed in an aqueous phase D, it being possible for the aqueous phases E and D to contain identical or different additives.

It has already been proposed to introduce water-soluble corticosteroids, especially hydrocortisone, into the encapsulated aqueous phase E of lipid vesicles, both into liposomes (International Application 87/07,502) or into nonionic vesicles (FR-A-2,315,991). However, since water-soluble corticosteroids are only slightly soluble in water, the amounts of corticosteroids encapsulable in the lipid vesicles are limited, and it is difficult to obtain a product having sufficient therapeutic efficacy.

It is known to dissolve fat-soluble corticosteroids in a lipid phase and to prepare an ointment by means of an oil-in-water or water-in-oil emulsion. These ointments are commonly used topically, but do not give satisfactory results for treatments necessitating high doses of corticosteroids, in particular, in this case too, as a result of the low solubilities of the active products.

It has also been proposed to introduce corticosteroids into the lipid lamellae of liposomes, and it is known that the product obtained has markedly enhanced therapeutic efficacy compared with an ointment in which the same corticosteroids are contained in a lipid in emulsion form. The lamellar structure of ionic lipid vesicles containing a fat-soluble corticosteroid hence improves the therapeutic efficacy of the corticosteroids.

According to the present invention, it found that, surprisingly, the therapeutic efficacy of corticosteroids is improved significantly further when the said corticosteroids are introduced into the lamellae of nonionic amphiphilic lipid visicles instead of introducing them into the lamellae of ionic amphiphilic lipid vesicles, that is to say of liposomes. It should be noted that it could in no way be predicted that a change in the ionic nature of the lipids used for the preparation of the vesicles would have an influence on the therapeutic efficacy of fat-soluble corticosteroids. The introduction of fat-soluble corticosteroids into the lamellae of nonionic vesicles hence enables a pharmaceutical composition to be obtained whose therapeutic efficacy is improved.

The subject of the present invention is hence a process for improving the therapeutic efficacy of fat-soluble corticosteroid(s), according to which the corticosteroid(s) is/are introduced into a amphiphilic lipid phase capable of forming, on dispersion in an aqueous phase, vesicles consisting of one or more lamella(e), and the said vesicles are formed in a known manner, characterized in that one (or more) nonionic lipid(s) is/are selected as amphiphilic lipid(s).

The fat-soluble corticosteroid(s) is/are preferably selected from the group composed of 17- and/or 21-mono- or -diesters of hydrocortisone, of cortisone, of prednisone, of prednisolone or of 6-methylprednisolone.

The corticosteroid(s) is/are selected more especially from:
hydrocortisone 21-acetate 17-propionate
hydrocortisone 17-butyrate
hydrocortisone 17-valerate
hydrocortisone 17-butyrate 21-propionate
cortisone 21-acetate
prednisone 21-acetate
prednisolone 21-acetate
6-methylprednisolone 21-acetate.

The nonionic amphiphilic lipids constituting the lamellae of the vesicles are preferably of the formula:

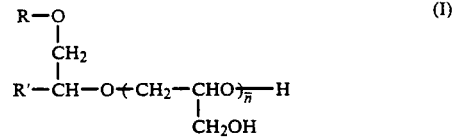 (I)

in which formula:
$\overline{n}$ is an average statistical value between 2 and 6;
R represents a radical $R_1$ or $R_2CO$, where $R_1$ is a linear or branched $C_{12}$–$C_{18}$ aliphatic radical and $R_2$ is a linear or branched $C_{11}$–$C_{17}$ aliphatic radical; and
R' represents a radical $R_1$ as defined above.

In a known manner, various additives may be allied with the nonionic amphiphilic lipids for the purpose of modifying the permeability or the surface charge of the vesicles. These additives are, in a known manner, long-chain alcohols and diols; sterols, more especially cholesterol and beta-sitosterol; long-chain amines and their quaternary ammonium derivatives, for example dodecyldimethylammonium bromide, or bis(hydroxyalkyl)amines; polyoxyethylenated fatty amines or their salts; esters of long-chain amino alcohols as well as their salts and quaternary ammonium derivatives; alkyl sulphates, for example sodium cetyl sulphate; and ionic derivatives of sterols, such as cholesteryl phosphate and sulphate.

In the context of the present invention, phosphoric esters of a fatty alcohol, for example dicetyl or dimyristyl phosphate or the corresponding sodium salts are especially suitable; these phosphoric esters may also be advantageously combined with cholesterol.

The allied additives represent less than 10% by weight of the nonionic amphiphilic lipids.

The corticosteroid(s) introduced into the lamellar lipid phase of the vesicles represent(s) from 0.5 to 2.5% by weight of the total lipids constituting the lamellae of the vesicles, that is to say of the nonionic lipids plus, where appropriate, the allied additives.

The vesicles preferably have average diameter of between 10 nm and 5,000 nm, and still more preferably between 10 and 1,000 nm.

The subject of the present invention is also, by way of a new product, a composition for carrying out the process according to the invention, consisting of nonionic amphiphilic lipid vesicles dispersed in an aqueous dispersion phase D, the vesicles having an average diameter of between 10 and 5,000 nm, and preferably between 10 and 1,000 nm, the corticosteroid(s) contained in the lamellar lipid phase being selected from the group composed of:

hydrocortisone 21-acetate 17-propionate
hydrocortisone 17-butyrate
hydrocortisone 17-valerate
hydrocortisone 17-butyrate 21-propionate
cortisone 21-acetate
prednisone 21-acetate
prednisolone 21-acetate
6-methylprednisolone 21-acetate and representing 0.5 to 2.5% by weight relative to the total lipids constituting the lamellae of the vesicles.

The lipids used are preferably selected from those of the formula:

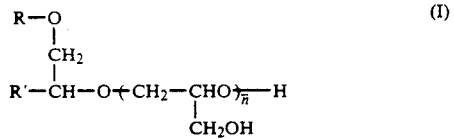

in which formula:

$\bar{n}$ is an average statistical value between 2 and 6;

R represents a radical $R_1$ or $R_2CO$, where $R_1$ is a linear or branched $C_{12}$–$C_{18}$ aliphatic radical and $R_2$ is a linear or branched $C_{11}$–$C_{17}$ aliphatic radical; and R' represents a radical $R_1$ as defined above.

The nonionic amphiphilic lipid is preferably allied with a phosphoric ester of a fatty alcohol, this ester preferably being dicetyl or dimyristyl phosphate or their salts, and especially the sodium salts. The phosphoric ester of a fatty alcohol is preferably allied with cholesterol.

According to the present invention, the aqueous phase D, in which the vesicles are dispersed, may be gelled. The vesicles may also be dispersed in an aqueous phase in the form of a dispersion of a water-immiscible liquid in an aqueous continuous phase, gelled or otherwise.

To obtain a gel, a gelling agent is added to the aqueous dispersion phase. Among usable gelling agents, cellulose derivatives, derivatives of algae or alternatively natural gums may be mentioned. By way of a gelling agent, it is preferable to use hydroxyethylcellulose or a polycarboxyvinyl acid such as, for example, "CARBOPOL 940" sold by the company "GOODRICH".

The gelling agent may be introduced in amounts of between 0.1 and 2% by weight relative to the total weight of the composition.

It is known from Patent FR-A-2,485,921 and 2,490,504 that nonionic amphiphilic lipid vesicles stabilize dispersions of water-immiscible liquids in an aqueous phase, without it being necessary to add an emulsifying agent. This property is utilized, adding a liquid immiscible with the aqueous dispersion phase D.

The water-immiscible liquid is preferably an oil. The oil used is advantageously selected from the group composed of esters of fatty acids and polyols, and esters of fatty acids and branched alcohols of formula $R_4$—COOR$_5$, in which $R_4$ represents a residue of a $C_8$–$C_{20}$ higher fatty acid and $R_5$ represents a $C_3$–$C_{20}$ branched hydrocarbon chain. If the oil is an ester of a fatty acid and a polyol, it is preferable for it to be selected from the group composed of sunflower, maize, soybean, marrow, grape-pip, sesame, macadamia, borage and blackcurrant oils and glyceryl tricaprocaprylate. If the oil is an ester of a higher fatty acid and a branched alcohol, it is preferable for it to be purcellin oil. Other vegetable oils may also be used, such as jojoba oil.

According to the invention, the water-immiscible liquid can also be a hydrocarbon or be a polysiloxane. The hydrocarbon is, for example, vaseline or liquid paraffin.

The amount of water-immiscible liquid amounts to at most 50% by weight relative to the total weight of the composition.

Other pharmaceutically acceptable water-soluble additives may be introduced into the dispersion phase D; they are preferably selected from the group composed of vitamins, hormones, bactericides, antioxidants, preservatives, chelating agents, opacifiers or colorings.

The water-soluble additives usable in the aqueous dispersion phase D may also be added to the encapsulated aqueous phase E, the additives contained in the phases E and D being identical or different.

The compositions according to the invention may be prepared by any know process for manufacturing nonionic lipid vesicles. The corticosteroid is added to the lipid mixture before performing the hydration of the said lipid mixture and forming the vesicles.

It is possible, for example, to use the process described in Patent FR-A-2,315,598. The nonionic amphiphilic lipid, the corticosteroid and, where appropriate, the allied additives are mixed at a temperature at least equal to the melting point of the mixture; the mixture obtained is brought into contact with the aqueous phase to be encapsulated and the resulting mixture is agitated so as to obtain a lamellar phase; an aqueous dispersion phase is then added, which phase is agitated so as to obtain the vesicles.

When a gelling agent or a water-immiscible liquid is added, these are added to the aqueous dispersion phase as described in Patent FR-A-2,485,921.

It is also possible to use the process described in U.S. Pat. No. 4,772,471. According to this process, the nonionic amphiphilic lipid, the corticosteroid and, where appropriate, the allied additive are dissolved in a solvent; the solvent is evaporated off in a rotary evaporator; the lipid film obtained is brought into contact with an aqueous phase; and the latter is dispersed with agitation to obtain the vesicles dispersed in an aqueous phase.

The gel and, where appropriate, the oil are added with agitation after the dispersion stage.

The compositions according to the invention may be used in a method of treatment of the human or animal body by therapy.

The examples given below, purely by way of illustration and without implied limitation, will permit a better understanding of the invention.

EXAMPLE 1 (Comparative)

(1) Preparation of the test compositions

The following were prepared:

a) A composition A according to the invention, in vesicular form, in which the lipid mixture constituting the vesicles has the following formulation (% by weight):
Nonionic lipid of formula

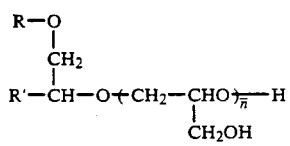 (I)

where
$\bar{n} = 6$
$R = C_{12}H_{25}$

| | |
|---|---|
| R' = $C_{14}H_{29}/C_{16}H_{33}$ | 8.5 g |
| Dimyristyl phosphate | 0.5 g |
| Hydrocortisone 21-acetate 17-propionate | 0.127 g |

This mixture is dispersed in 58 g of water so as to obtain vesicles of average diameter 200 nm. 15 g of liquid paraffin are then added in order to obtain a fine dispersion. 16 g of an aqueous pregel containing 0.42 g of a polycarboxyvinyl acid sold under the tradename "CARBOPOL 940" are then introduced. The preparation is finally neutralized with 0.35 g of pure triethanolamine. It is made up with the amount of water sufficient for 100 g.

b) A composition B not forming part of the invention in vesicular form, in which the lipid mixture constituting the vesicles has the following formulation (% by weight):

| | |
|---|---|
| Ionic lipid consisting of soybean phospholipids, sold by the company "LUCAS MEYER" under the name "EPIKURON 145 V" | 10 g |
| Hydrocortisone 21-acetate 17-propionate | 0.127 g |

This mixture is dispersed in 58 g of water so as to obtain vesicles of average diameter 200 nm. 15 g of liquid paraffin are then added in order to obtain a fine dispersion. 16 g of an aqueous pregel containing 0.42 g of a polycarboxyvinyl acid sold under the tradename "CARBOPOL 940" are then introduced. The preparation is finally neutralized with 0.35 g of pure triethanolamine. It is made up with the amount of water sufficient for 100 g.

c) An oil-in-water emulsion C (not forming part of the invention) of the following formulation:

| | |
|---|---|
| Liquid paraffin | 15 g |

| -continued | |
|---|---|
| Mixture of glyceryl stearate and polyethylene glycol stearate containing 100 moles of ethylene oxide, marketed by the company "ICI AMERICAS" under the name "ARLACEL 165" | 3 g |
| Stearyl alcohol | 1 g |
| Polyethylene glycol stearate containing 50 moles of ethylene oxide, marketed by the company "ICI AMERICAS" under the name "MYRJ 53" | 3 g |
| Hydrocortisone 21-acetate 17-propionate | 0.127 g |
| Water q.s. | 100 g |

The oil phase is dispersed in 77.6 g of water containing 0.42 g of a polycarboxyvinyl acid sold under the tradename "CARBOPOL 940", so as to obtain an oil-in-water emulsion in which the droplets have an average diameter of 3,000 nm. The preparation is finally neutralized with 0.3 g of triethanolamine.

(2) Description of the tests

According to this test, an application of the three compositions A, B and C is made on the inner and outer surfaces of the right ear of a rat. One hour later, a solution of croton oil is applied. Six hours after this application, both ears are removed and then weighed.

From a control batch and a treated batch, the percentage inhibition due to the test product is calculated.
The results are given in Table I below.

TABLE I

| Composition | Inhibition of oedema (in %) |
|---|---|
| A | 85 |
| B | 78 |
| C | 50 |

These trials show that the composition A, in which the corticosteroid is in the lipid lamellae of nonionic vesicles, has a markedly higher anti-inflammatory action than that of the composition B, in which the corticosteroid is in the lipid lamellae of liposomes, and than that of the composition C, in which the corticosteroid is in the dispersed phase of an oil-in-water emulsion.

EXAMPLE 2

A composition in gel form having the following formulation (by weight) is prepared:

| | |
|---|---|
| Lipid vesicles comprising: Nonionic lipid of formula (I) (9.50%) | 10.95 g |

$$\begin{array}{c} R-O \\ | \\ CH_2 \\ | \\ R'-CH-O+CH_2-CHO\overline{)_{\bar{n}}}H \\ | \\ CH_2OH \end{array} \quad (I)$$

where
$\bar{n} = 6$
$R = C_{12}H_{25}$
$R' = C_{14}H_{29}/C_{18}H_{33}$
Dimyristyl phosphate (0.50%)
Cholesterol (0.95%)

| | |
|---|---|
| Hydrocortisone 21-acetate 17- | 0.13% |

| | |
|---|---|
| -continued | |
| propionate | |
| Sodium salt of ethylenediaminetetra-acetic acid (EDTA) | 0.05% |
| Polycarboxyvinyl acid sold by the company "GOODRICH" under the tradename "CARBOPOL 940" | 0.42% |
| Triethanolamine | 0.4% |
| Preservatives | 0.1% |
| Purified water q.s. | 100% |

To prepare the composition, the nonionic lipid of formula (I), cholesterol, dimyristyl phosphate and hydrocortisone 21-acetate 17-propionate are mixed by melting. The lipid mixture obtained is then hydrated with water to which the disodium salt of ethylenediaminetetraacetic acid has been added. The mixture is agitated to obtain the vesicles. The "CARBOPOL 940" gel containing the preservatives is then added and dispersed. Finally, the pH of the mixture is adjusted to a value of 5 by adding triethanolamine. It has been checked by microscopy that crystals of corticosteroid are absent from the aqueous dispersion phase D, that is to say the corticosteroid is properly included in the vesicular lipids.

This composition is used at the rate of two topical applications per day (100 mg/cm²) for the treatment of a subject suffering from corticoid-sensitive eczematous lesions for a period of 7 days, and a significant improvement is noted in the inflammatory state of the treated areas.

EXAMPLE 3

A cream having the following formulation (% by weight) is prepared:

| | |
|---|---|
| Lipid vesicles comprising: | 10% |
| Nonionic lipid of Example 2 (9.5%) | |
| Dimyristyl phosphate (0.5%) | |
| Hydroxycortisone 17-butyrate | 0.1% |
| Disodium salt of ethylenediamine-tetraacetic acid | 0.05% |
| Polycarboxyvinyl acid sold by the company "GOODRICH" under the tradename "CARBOPOL 940" | 0.42% |
| Triethanolamine | 0.4% |
| Liquid paraffin | 15.00% |
| Preservatives | 0.1% |
| Purified water q.s. | 100% |

The composition is prepared in the following manner. The vesicular lipids and hydrocortisone 17-butyrate are mixed by melting. The lipid mixture obtained is hydrated with purified water to which the disodium salt of ethylenediaminetetraacetic acid has been added. The mixture is homogenized by agitation with a turbo-mixer so as to obtain the dispersion of lipid vesicles in an aqueous phase. The liquid paraffin is added and dispersed. The "CARBOPOL 940" containing the preservatives is then introduced. Finally, the preparation is neutralized with triethanolamine.

This composition is used at the rate of two topical applications per day (100 mg/cm²) for the treatment of a subject suffering from psoriasis for a period of 10 days, and a significant improvement is noted in the squamous inflammatory lesions.

We claim:

1. A process for improving the therapeutic efficacy of a corticosteroid by incorporating said corticosteroid in the lamellae of vesicles formed from a nonionic amphiphilic lipid, said corticosteroid being selected from the group consisting of hydrocortisone 21-acetate 17-propionate, said process comprising
   (a) introducing said corticosteroid into a nonionic amphiphilic lipid constituting the lamellae of vesicles formed on dispersing said nonionic amphiphilic lipid in an aqueous phase so as to form a nonionic amphiphilic lipid phase, said nonionic amphiphilic lipid having the formula

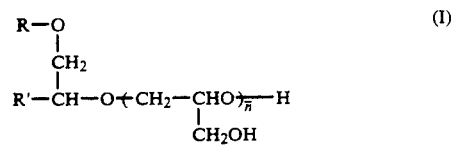

wherein
   $\bar{n}$ has an average statistical value between 2 and 6;
   R represents $R_1$ or $R_2CO$, wherein $R_1$ is a linear or branched $C_{12}$-$C_{14}$ aliphatic radical and $R_2$ is a linear or branched $C_{11}$-$C_{17}$ aliphatic radical, and
   R' represents $R_1$ as defined as above, and
   dispersing the resulting nonionic amphiphilic lipid phase in an aqueous phase so as to form said vesicles, said coritcosteroid representing 0.5 to 2.5 by weight relative to the total weight of the lipids constituting the lamellae of said vesicles.

2. The process of claim 1 wherein said nonionic amphiphilic lipid is associated with a phosphoric ester of a fatty alcohol.

3. The process of claim 2 wherein said phosphoric ester of a fatty alcohol is dicetyl or dimyristyl phosphate or the corresponding sodium salts.

4. The process of claim 2 wherein said phosphoric ester of a fatty alcohol is associated with cholesterol.

5. The process of claim 1 wherein said vesicles have an average diameter ranging from 10 to 5,000 nm.

6. A composition comprising an aqueous dispersion of nonionic amphiphilic lipid vesicles having an average diameter ranging from 10 to 5,000 nm, the lamellae of said vesicles comprising (i) a nonionic amphiphilic lipid having the formula

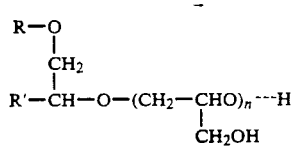

wherein
$n$ has an average statistical value between 2 and 6;
R represents $R_1$ or $R_2CO$, wherein $R_1$ is a linear or branched $C_{12}$-$C_{14}$ aliphatic radical and $R_2$ is a linear or branched $C_{11}$-$C_{17}$ aliphatic radical, and
R' represents $R_1$ as defined above, and
(ii) the corticosteroid hydrocortisone 21-acetate 17-propionate, said corticosteroid being present in an amount ranging from 0.5 to 2.5 percent by weight relative to the total weight of the lipids constituting the lamellae of said vesicles.

7. The composition of claim 6 wherein said nonionic amphiphilic lipid is associated with a phosphoric ester of a fatty alcohol.

8. The composition of claim 7 wherein the phosphoric ester of a fatty alcohol is dicetyl or dimyristyl phosphate or the corresponding sodium salts.

9. The composition of claim 7 wherein said phosphoric ester of a fatty alcohol is associated with cholesterol.

10. The composition of claim 6 wherein said aqueous dispersion is a dispersion of a water immiscible liquid in a continuous aqueous phase.

11. The composition of claim 10 wherein said aqueous dispersion is gelled.

12. The composition of claim 11 which includes a gelling agent selected from the group consisting of a cellulose derivative, a derivative of algae and a natural gum.

13. The composition of claim 10 wherein said water immiscible liquid is an oil.

14. The composition of claim 13 wherein said oil is an ester of a fatty acid and a polyol or an ester of a fatty acid and a branched alcohol, said ester having the formula $R_4$—COOR$_5$ wherein $R_4$ represents the residue of a $C_8$-$C_{20}$ higher fatty acid and $R_5$ represents a $C_3$-$C_{20}$ branched hydrocarbon chain.

15. The composition of claim 10 wherein said water immiscible liquid is a hydrocarbon, a polysiloxane or jojoba oil.

16. The composition of claim 6 wherein said nonionic amphiphilic lipid vesicles encapsulate an aqueous phase.

17. The composition of claim 6 wherein said aqueous dispersion contains at least one pharmaceutically acceptable water-soluble additive.

18. The composition of claim 17 wherein said water-soluble additive is selected from the group consisting of a vitamin, a hormone, a bactericide, an antioxidant, a preservative, a chelating agent, an opacifier and a coloring agent.

19. The composition of claim 16 wherein said aqueous phase encapsulated in said nonionic amphiphilic lipid vesicles contains at least one pharmaceutically acceptable water-soluble additive.

20. The composition of claim 19 wherein said water-soluble additive is selected from the group consisting of a vitamin, a hormone, a bactericide, an antioxidant, a preservative, a chelating agent, an opacifier and a coloring agent.

21. A method for the therapeutic treatment of a human or animal body comprising applying thereto an effective amount of the composition of claim 6.

* * * * *